United States Patent [19]

Tsuchiya et al.

[11] 4,297,410
[45] Oct. 27, 1981

[54] ABSORBENT MATERIAL

[75] Inventors: Yoshimi Tsuchiya, Utsunomiya; Masayuki Sagae, Tochigi; Hiroshi Mizutani, Yachiyo, all of Japan

[73] Assignee: Kao Soap Co., Ltd., Tokyo, Japan

[21] Appl. No.: 81,234

[22] Filed: Oct. 2, 1979

[30] Foreign Application Priority Data

Oct. 12, 1978 [JP] Japan ................................. 53-140165

[51] Int. Cl.$^3$ ................................................ B32B 5/16
[52] U.S. Cl. ................................ 428/283; 128/290 R; 156/283; 428/286; 428/913
[58] Field of Search ............... 428/198, 202, 211, 286, 428/195, 296, 283, 913; 128/284, 285, 287, 290 R; 156/283

[56] References Cited

U.S. PATENT DOCUMENTS

| | | | |
|---|---|---|---|
| 3,888,256 | 6/1975 | Studinger | 128/290 R |
| 3,900,378 | 8/1975 | Yen et al. | 128/284 |
| 3,901,236 | 8/1975 | Assarsson et al. | 128/290 R |
| 3,971,379 | 7/1976 | Chatterjee | 128/290 R |
| 4,055,180 | 10/1977 | Karami | 128/287 |
| 4,055,184 | 10/1977 | Karami | 128/287 |
| 4,058,124 | 11/1977 | Yen et al. | 128/284 |
| 4,102,340 | 7/1978 | Masek et al. | 128/287 |
| 4,187,342 | 2/1980 | Holst et al. | 428/913 |

Primary Examiner—James J. Bell
Attorney, Agent, or Firm—Blanchard, Flynn, Thiel, Boutell & Tanis

[57] ABSTRACT

An absorbent material companies a non-woven fabric including thermoplastic fibers, on which a highly absorbing, hydrophilic polymetric substance is scattered and which is thermally set.

7 Claims, 2 Drawing Figures

ABSORBENT MATERIAL

BACKGROUND OF THE INVENTION

1. Field of the Invention

The present invention relates to an absorbent material which is used for the manufacture of sanitary napkins, body fluid-absorbing medicinal pads and the like.

2. Description of Prior Art

As the absorbent material for these absorbent products, there have heretofore been used cotton fabrics, rayon-cotton fabrics, cotton-like pulps and absorbent papers. However, in these conventional absorbent materials, the absorbing capacity per unit weight is very small. Accordingly, the final products become bulky and handling is very troublesome, and disposal of the used products causes problems.

Recently, there have been made various proposals in utilization of various polymers as the highly absorbing substance for the manufacture of absorbent materials. However, no satisfactory absorbent material has been developed.

We made researches with a view to developing an absorbent material in which the foregoing defects involved in the conventional absorbent materials are eliminated, and as a result, we have now completed the present device.

BRIEF DESCRIPTION OF THE DRAWINGS

The drawings illustrate embodiments of the present invention, in which.

SUMMARY OF THE INVENTION

More specifically, in accordance with the present invention, there is provided an absorbent material comprising a non-woven fabric including thermoplastic fibers, on which a highly absorbing, hydrophilic polymeric substance is scattered and which is thermally set.

In the absorbent material of the present invention, since particles of a highly absorbing, hydrophilic polymeric substance are applied to a non-woven fabric including thermoplastic fibers so that the particles are not moved or let to fall down from the non-woven fabric, the water absorbing capacity of the absorbent material of the present invention is several times as high as the water absorbing capacity of an absorbent material composed solely of the non-woven fabric. Furthermore, the absorbent material of the present invention is rich in the softness and therefore, it can easily be assembled into various absorbent products.

As the highly absorbing, hydrophilic polymeric substance that is used in the present invention, there can be mentioned, for example, ethylene oxide polymers, acrylic acid type polymers, cellulose derivatives, and other synthetic polymers such as polyvinyl alcohol. A polymer capable of absorbing water in an amount at least 30 times the weight of the polymer is preferably employed.

As the non-woven fabric including thermoplastic fibers, that is used in the present invention, there can be mentioned, for example, an absorbent paper or rayon paper containing 10 to 50% by weight of fibers of a polyolefin such as polyethylene or polypropylene. From the viewpoint of the softness, a non-woven fabric having a unit weight of 10 to 40 g/m$^2$ is preferred.

The absorbent material of the present invention can easily be prepared by scattering particles of a highly absorbing, hydrophilic polymeric substance onto the abovementioned non-woven fabric and heating or pressing the nonwoven fabric at a temperature melting the thermoplastic fibers constituting the non-woven fabric.

In the absorbent material of the present invention, a similar non-woven fabric may be piled on the hydrophilic polymeric substance applied to the non-woven fabric including thermoplastic fibers, or in some application fields, it is possible to laminate an ordinary absorbent paper or cotton-like pulp on the absorbent material of the present invention and heat-treat the assembly to form a sheet-like product.

The present invention will now be described in detail by reference to the following Examples.

EXAMPLE 1

Figure 1:
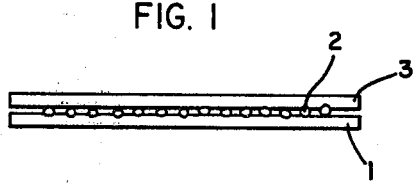
FIG. 1 is a sectional view showing the absorbent material prepared in Example 1 and FIG. 2 is a sectional view showing the absorbent material prepared in Example 3.

As shown in FIG. 1, poly(sodium acrylate) 2 was scattered on an absorbent paper 1 (having a unit weight of 20 g/m$^2$) containing 20% of polyethylene in an amount of 25 g/m$^2$, and an absorbent paper 3 (having a unit weight of 25 g/m$^2$) was piled thereon. The assembly was heat-pressed to prepare an absorbent material.

EXAMPLE 2

A starch-acrylonitrile saponified product was scattered in an amount of 20 g/m$^2$ on an absorbent paper (having a unit weight of 25 g/m$^2$) containing 30% of polypropylene, and an absorbent paper (having a unit weight of 30 g/m$^2$) was piled thereon. The assembly was heat-pressed to prepare an absorbent material.

EXAMPLE 3

Figure 2:
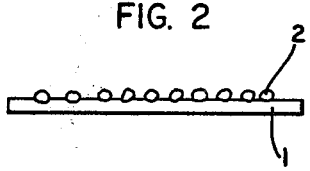

As shown in FIG. 2, sodium carboxymethyl cellulose 2 was scattered in an amount of 30 g/m$^2$ onto an absorbent paper 1 (having a unit weight of 30 g/m$^2$) containing 30% of polyethylene, and the cellulose-applied absorbent paper was heated to prepare an absorbent material.

EXAMPLE 4

Polyethylene oxide was scattered in an amount of 20 g/m$^2$ onto a rayon paper containing 30% of polyethylene/polypropylene (50/50), and a similar rayon paper was piled thereon. The assembly was heat-pressed to prepare an absorbent material.

EXAMPLE 5

A sodium acrylate-acrylamide copolymer was scattered in an amount of 15 g/m$^2$ onto a rayon paper (having a unit weight of 20 g/m$^2$) containing 20% of polyethylene, and an absorbent paper (having a unit weight of 25 g/m$^2$) was further piled thereon. The assembly was heat-pressed to prepare an absorbent material.

The water-absorbing capacities of the absorbent materials prepared in Examples 1 through 5 and cotton-like pulp and absorbent paper as comparative absorbent materials were measured to obtain results shown in Table 1, from which it will readily be understood that each of the absorbent materials according to the present device has an excellent water-absorbing property.

TABLE 1

| | Water absorption* ratio under no pressure | Water absorption ratio* under pressure of 50 g/cm$^2$ |
|---|---|---|
| Example 1 | 30 | 20 |
| Example 2 | 32 | 30 |
| Example 3 | 18 | 15 |
| Example 4 | 25 | 22 |
| Example 5 | 16 | 19 |
| Cotton-like pulp | 12 | 2 |
| Absorbent paper | 14 | 2 |

Note

The water absorption ratio is defined by the following formula:

$$\text{Water absorption ratio} = \frac{\text{amount (g) of absorbed water}}{\text{amount (g) of absorbent material}}$$

What is claimed is:

1. An absorbent material consisting essentially of: a first, non-woven fabric, absorbent sheet consisting essentially of absorbent fibers capable of absorbing exudations from the human body and from 10 to 50% by weight of thermoplastic polyolefin fibers; a multitude of particles deposited on one surface of said first sheet so as to form a discrete layer of said particles on said one surface of said first sheet wherein said particles project upwardly above said one surface of said first sheet, said particles consisting essentially of hydrophilic polymeric substance capable of absorbing water in an amount at least 30 times the weight of said hydrophilic polymeric substance, said particles being meltadhered to said thermoplastic polyolefin fibers of said first sheet at the locations where said particles contact said thermoplastic polyolefin fibers, said absorbent material having been prepared by depositing said particles on said sheet and then heating said sheet to melt thermoplastic polyolefin fibers therein whereby to cause said particles to adhere to said thermoplastic polyolefin fibers.

2. An absorbent material as claimed in claim 1 including a second, non-woven fabric, absorbent sheet laminated on and adhered to said layer of particles and located on the opposite side of said layer from said first sheet, said second sheet extending substantially parallel with and being upwardly spaced from said first sheet.

3. An absorbent material as claimed in claim 1 or claim 2 in which said first, non-woven fabric, absorbent sheet has a unit weight of from 10 to 40 g/m$^2$.

4. A process for preparing an absorbent material, which comprises the steps of:
scattering particles of a highly absorbent, hydrophilic polymer substance capable of absorbing water in an amount at least 30 times the weight of the polymer substance onto a nonwoven absorbent fabric comprising polyolefin fibers and cellulose fibers and then heating said non-woven fabric to fix said particles thereon.

5. A process as claimed in claim 4, in which the heating step is conducted at a temperature at which said polyolefin fibers are melted.

6. A process as claimed in claim 4, wherein said non-woven fabric consists of 10 to 50 wt. % of polyolefin fibers and 90 to 50 wt. % of cellulose fibers, said fabric having a unit weight of 10 to 40 g/cm$^2$.

7. A process as claimed in claim 4 which comprises the additional steps of placing a sheet of absorbent paper on said non-woven fabric on which said particles of the highly absorbing, hydrophilic polymer substance have been scattered and heat pressing the resulting assembly.

* * * * *